Figure 1:
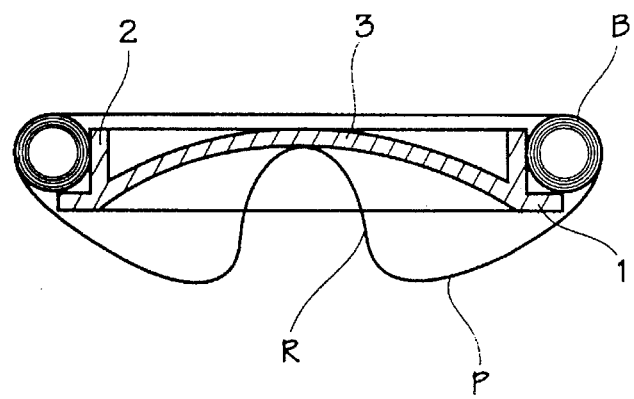

United States Patent [19]
Babled

[11] Patent Number: 5,479,940
[45] Date of Patent: Jan. 2, 1996

[54] SECURING AND PROTECTIVE RIGID DISC FOR CONDOM; CONDOM PROVIDED WITH SUCH A DISC

[76] Inventor: Raymond G. Babled, 72, avenue d'Orgeavl, 95210 Saint-Gratien, France

[21] Appl. No.: 232,106

[22] PCT Filed: Jul. 20, 1993

[86] PCT No.: PCT/FR93/00737

§ 371 Date: Apr. 21, 1994

§ 102(e) Date: Apr. 21, 1994

[87] PCT Pub. No.: WO94/05237

PCT Pub. Date: Mar. 17, 1994

[30] Foreign Application Priority Data

Aug. 28, 1992 [FR] France ................................ 92 10353

[51] Int. Cl.$^6$ ........................................................ A61F 6/04
[52] U.S. Cl. ............................. 128/844; 128/842; 206/69
[58] Field of Search ..................... 128/844, 842, 128/918; 206/69; 604/349, 347, 350, 351, 352, 346

[56] References Cited

U.S. PATENT DOCUMENTS

| | | | |
|---|---|---|---|
| 2,904,041 | 9/1959 | Brown | 128/132 |
| 4,726,359 | 2/1988 | Schroeder | 604/349 |
| 4,738,357 | 4/1988 | Martin et al. | 604/349 |
| 4,875,491 | 10/1989 | Parrone | 128/844 |
| 5,163,449 | 11/1992 | van der Valk | 128/844 |
| 5,211,640 | 5/1993 | Wendler | 604/349 |
| 5,316,019 | 5/1994 | Jones | 128/844 |

FOREIGN PATENT DOCUMENTS

| | | | |
|---|---|---|---|
| 580470 | 1/1994 | European Pat. Off. | 604/349 |
| WO90/12554 | 11/1990 | France . | |
| 2661819 | 11/1991 | France | 128/844 |
| 2693652 | 1/1994 | France | 128/844 |
| 3902093 | 1/1989 | Germany . | |
| 8914151 | 12/1989 | Germany . | |
| 3902093 | 8/1990 | Germany | 128/918 |
| 7802424 | 10/1979 | Sweden | 604/349 |
| 8802624 | 4/1988 | WIPO . | |
| 9206657 | 4/1992 | WIPO | 128/844 |
| 9321873 | 11/1993 | WIPO | 128/844 |

*Primary Examiner*—Robert A. Hafer
*Assistant Examiner*—Michael O'Neil
*Attorney, Agent, or Firm*—W. Thad Adams, III

[57] ABSTRACT

Securing and protective rigid disc for a condom, having on its peripheral edge a flat flange 1 provided to be engaged under the bead B of the sheath of condom P, said disc being placed on the upper and outside end of the condom. The flange 1 surrounds a part of the disc which, towards the outside, presents a protrusion above the plane of said flange. This protrusion preferably comprises a skirt 2 serving of lateral backing for the bead of the sheath and surrounding a convex dom 3, for example of spherical shape. This disc can be used with all kind of condoms.

19 Claims, 1 Drawing Sheet

SECURING AND PROTECTIVE RIGID DISC FOR CONDOM; CONDOM PROVIDED WITH SUCH A DISC

This application is a national stage application, according to Chapter II of the Patent Cooperation Treaty. This application claims the priority date of Aug. 28, 1992 for French Patent No. 92 10353.

The present invention relates to a securing and protective rigid disc for a condom, the peripheral edge of said disc being designed to be introduced under the rolled bead of the sheath, said disc being positioned on the upper end and on the outside of the sheath.

A condom provided with such a disc has been disclosed in the BABLED French patent application No. 90-05994 filed on May 14, 1990. It is essentially a question of a flat disc. Its object is to avoid that the preservative be erroneously put by a user in the wrong direction. The object of such a disc is even to prevent pathogenic germs to be transmitted by the user to his partner when he puts the condom in the right direction after a first attempt when, positioning it in the wrong direction, he has put the normal outside end of the preservative into contact with the glans of his penis. This kind of disc has therefore a double function: it is a securing and protective disc.

The object of the present invention is to improve such a disc, particularly by making safer its bearing in the bead of the condom up to the moment immediately preceding its positioning, this while allowing a very easy ejection of the disc, needing no intervention of the user, this ejection automatically happening at the very beginning of the putting in place.

To this end, the present invention relates to a protective rigid disc for a condom, said disc presenting on its peripheral edge a flat flange designed to be engaged under the rolled bead of the sheath, said disc being positioned on the upper end and on the outside of said sheath, characterized in that said flange surrounds a part of the disc which presents towards the outside a protrusion extending above the plane of said flange.

This protrusion cooperates, together with the flange, to the centering and positioning of the disc in the bead of the sheath. This protrusion extending towards the outside with respect to the plane of the flange, will also allow the user to immediatly realize by touch, even in the darkness, whether he holds the condom in the right position, or if he must turn it inside out before putting it in place.

The protrusion of the disc can take all the possible shapes, allowing it to fulfil the same functions. Said protrusion can particularly consist of a skirt forming a lateral backing for the bead, this skirt having for example a height of 4–5 mm. The protrusion in question could also be constituted of a hood convex towards outside, that is to say a kind of dome having the shape of a sphere or similar, the base of which would connect to the flange. The protrusion of the disc can also consist both of the skirt and of said convex hood, in which case the hood, advantageously connected, by its peripheral edge, to the base of the skirt, can have essentially the same height as this skirt, or be slightly higher than this one; therefore, the hood will be able, in such a case, to appear slightly in protrusion above the edge of the skirt, and so to cooperate for helping the user to recognize by touch the right direction of positioning.

As concerns the flange, that is to say the flat part of the disc which extends all around said protrusion, it will have any width and shape allowing it to be sufficiently inserted under the bead of the condom in order that the disc does not risk to escape from it by chance in the packing, or prematurely before the instant immediatly preceding the positioning onto the penis. To this end, the width of the flange can be of about 1.2–2.5 mm, these values being given only as an indication.

If in a plan view the disc has a circular shape, as this will be the most current case, the skirt will also have a circular shape, so that the flange, itself also circular in shape, will have a constant width. This flange can be continuous or interrupted. In that case, it can be constituted for example of a series of points, that is to say of small radial protrusions, equally spaced on the periphery of the skirt.

Figure 2:
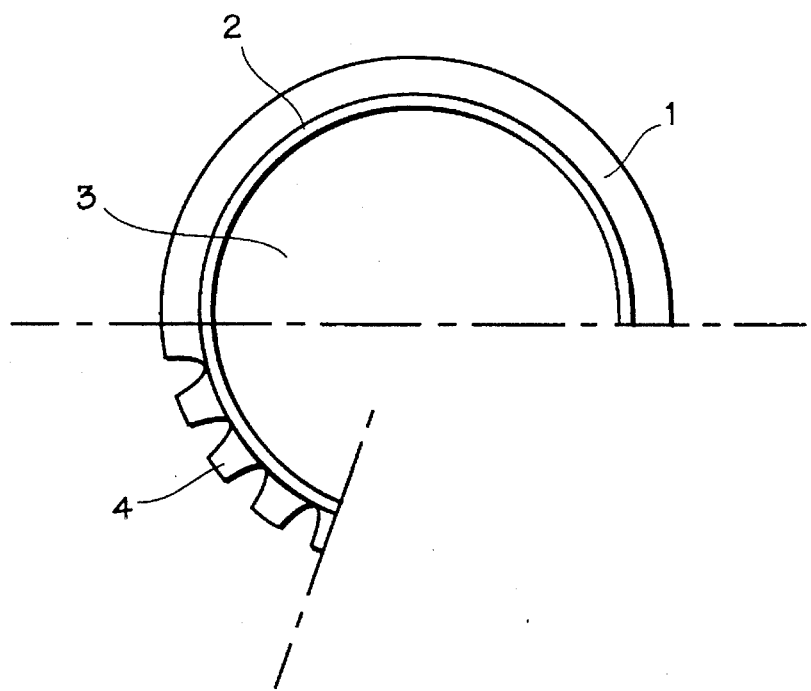
Figure 3:
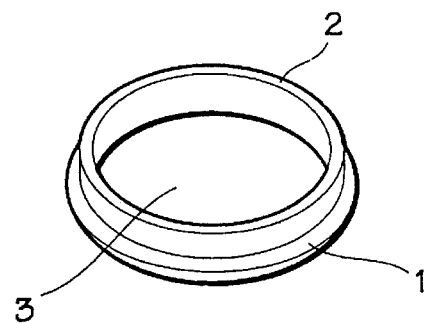

An embodiment of the invention will now be disclosed by way of a non limitative example, with reference to the figures of the appended drawing in which:

FIG. 1 is an axial section of a rolled condom provided with a rigid disc in accordance with the invention;

the upper part of FIG. 2 shows the shape of the disc alone, in a plan view, and the lower part of this figure shows a variant for the shape of the flange; and FIG. 3 is a perspective view of the disc in a reduced scale.

On the different figures, the flange of the securing and protective rigid disc has been referenced 1, the lateral backing skirt 2, and the convex hood 3. The disc being circular in shape in this example, it is understood that the skirt 2 is cylindrical, the convex hood or dome 3 being spherical or of similar shape. It is seen that the disc is securely maintained in the bead B of condom P, and is supported under that bead by its flange 1 and laterally against this bead by its skirt 2. In that example, it has been supposed that the condom P is provided with a reservoir R. It can be seen that this reservoir is easily lodged inside dome 3.

The upper part of FIG. 2 shows a flange 1 of circular shape and of constant width. At the lower part of this figure, the possibility has been shown to give it the shape of a series of points 4 equally spaced around skirt 2.

The outside diameters of the flange 1 and of the skirt 2 are of course determined by taking into account the inside diameter of the bead B of a condom having normal dimensions, in order that the outside diameter of the skirt be slightly greater than the internal diameter of the bead; so, the condom will be slightly stretched radially by the operation of putting the disc into place, which will assume an excellent bearing of that disc. So, a usual outside diameter for skirt 2 will be of about 28 mm with a diameter of flange 1 of about 31 to 32 mm, these values being again given only as an indication.

Skirt 2 may have a height of about 4 mm, and the convex hood 3 a height of about 5 mm.

The convex hood 3, normally spherical, will have a radius of curvature adapted to the one of skirt 2. For a skirt having an outside diameter for example comprised between 26 and 30 mm, and therefore with a diameter of flange 1 comprised between about 30 and 35 mm, the radius of curvature of hood 3 will be of about 20 to 25 mm.

The advantage of such a spherical hood 3 is, as indicated above, to make easier for the user to recognize the direction in which he must present the condom before putting it onto his penis; it is obvious that he will position it in such a way that the concave face of the hood of the disc covers the glans. This gesture will rapidly become so natural that it will be made as by reflex, without requiring any particular attention. It will also be understood that the ejection of the disc will also occur naturally, without demanding any particular intervention, the condom being put into place in the usual way, by making the bead B going down along the penis. As from the beginning of the unrolling, the disc, having played its role of security and of protection, will be automatically ejected.

The disc according to the invention also presents the advantage that it can be easily positioned by the manufacturer in a mass production. By stiffening the condoms, the discs will make it easier to package them as well as to hold them in the packages, when these ones are constituted of square sealed pockets or of any other shape.

The material constituting the discs will preferably be polyethylene of alimentary quality, or all other convenient synthetic material.

I claim:

1. In combination with a rolled condom in rolled form defining inner and outer annular side walls, and open and closed ends thereof, a securing and protective rigid insert for being removably positioned within the open end of the rolled condom to ensure proper unrolling and application of the condom by a user, said insert comprising:
   (a) a cylindrical ring for engaging the inner side wall of the rolled condom;
   (b) a radially and outwardly extending flat flange formed to a bottom peripheral edge of said ring, and residing under the inner side wall of the rolled condom between the open end thereof and the closed end thereof;
   (c) a solid wall hood formed to said ring and enclosing an open area defined by said ring;
   (d) said ring, flange, and hood defining a unitary structure, whereby:
      (1) upon proper application of the rolled condom by the user, the insert automatically separates from the condom as the condom is unrolled; and
      (2) upon attempting improper application of the rolled condom, the insert prevents unrolling of the condom by the user (e) wherein the solid wall hood is convex having a hollow side which is on the same side of the insert as said flange.

2. A combination according to claim 1, wherein the cylindrical ring includes an outer surface defining a lateral backing for the rolled condom in rolled form.

3. A combination according to claim 2, wherein said cylindrical ring has a height of 4–5 mm, and an outside diameter of 26–30 mm.

4. A combination according to claim 1, wherein an apex of the convex, solid wall hood is equal to the height of said cylindrical ring.

5. A combination according to claim 1, wherein an apex of the convex, solid wall hood is slightly greater than the height of said cylindrical ring.

6. A combination according to claim 1, wherein the flange has a lateral width of between 1.2 and 2.5 mm.

7. A combination according to claim 1, wherein the flange is annular having an outside diameter of between 30 and 35 mm.

8. A combination according to claim 1, wherein the flange defines a plurality of serrations formed around a periphery thereof.

9. A combination according to claim 1, wherein said convex, solid wall hood has a radius of curvature of between 20–25 mm.

10. A combination according to claim 1, wherein said insert is formed of polyethylene of alimentary quality.

11. A securing and protective rigid insert for use with a rolled condom in rolled form defining inner and outer annular side walls, and open and closed ends thereof, said insert being removably positioned within the open end of the rolled condom to ensure proper unrolling and application of the condom by a user, said insert comprising:
    (a) a cylindrical ring for engaging the inner side wall of the rolled condom;
    (b) a radially and outwardly extending flat flange formed to a bottom peripheral edge of said ring, and residing under the inner side wall of the rolled condom between the open end thereof and the closed end thereof;
    (c) a solid wall hood formed to said ring and enclosing an open area defined by said ring;
    (d) said ring, flange, and hood defining a unitary structure, whereby:
       (1) upon proper application of the rolled condom by the user, the insert automatically separates from the condom as the condom is unrolled; and
       (2) upon attempting improper application of the rolled condom, the insert prevents unrolling of the condom by the user (e) wherein the solid wall hood is convex having a hollow side which is on the same side of the insert as said flange.

12. A securing and protective rigid insert according to claim 11, wherein said cylindrical ring has a height of 4–5 mm, and an outside diameter of 26–30 mm.

13. A securing and protective rigid insert according to claim 11, wherein an apex of the convex, solid wall hood is equal to the height of said cylindrical ring.

14. A securing and protective rigid insert according to claim 11, wherein an apex of the convex, solid wall hood is slightly greater than the height of said cylindrical ring.

15. A securing and protective rigid insert according to claim 11, wherein the flange has a lateral width of between 1.2 and 2.5 mm.

16. A securing and protective rigid insert according to claim 11, wherein the flange is annular having an outside diameter of between 30 and 35 mm.

17. A securing and protective rigid insert according to claim 11, wherein the flange defines a plurality of serrations formed around a periphery thereof.

18. A securing and protective rigid insert according to claim 11, wherein said convex, solid wall hood has a radius of curvature of between 20–25 mm.

19. A securing and protective rigid insert according to claim 11, wherein said insert is formed of polyethylene of alimentary quality.

* * * * *